US012700492B2

(12) United States Patent
Traneus et al.

(10) Patent No.:  US 12,700,492 B2
(45) Date of Patent:  Aug. 4, 2026

(54) OPTIMIZATION OF THERMORADIOTHERAPY TREATMENT

(71) Applicant: RaySearch Laboratories AB (Publ), Stockholm (SE)

(72) Inventors: Erik Traneus, Uppsala (SE); Albin Fredriksson, Stockholm (SE); Kjell Eriksson, Balsta (SE); Jakob Odén, Sollentuna (SE)

(73) Assignee: Raysearch Laboratories AB (publ), Stockholm (SE)

( * ) Notice: Subject to any disclaimer, the term of this patent is extended or adjusted under 35 U.S.C. 154(b) by 157 days.

(21) Appl. No.: 18/555,004

(22) PCT Filed: Apr. 13, 2022

(86) PCT No.: PCT/EP2022/059879
§ 371 (c)(1),
(2) Date: Oct. 12, 2023

(87) PCT Pub. No.: WO2022/228899
PCT Pub. Date: Nov. 3, 2022

(65) Prior Publication Data
US 2024/0221899 A1      Jul. 4, 2024

(30) Foreign Application Priority Data

Apr. 27, 2021    (EP) ..................................... 21170669

(51) Int. Cl.
*G16H 20/40*          (2018.01)
*A61N 5/10*           (2006.01)

(52) U.S. Cl.
CPC ........... *G16H 20/40* (2018.01); *A61N 5/1038* (2013.01)

(58) Field of Classification Search
None
See application file for complete search history.

(56) References Cited

U.S. PATENT DOCUMENTS

2002/0102216 A1*  8/2002  Lanza .................. A61K 49/226
                                              424/130.1
2014/0149092 A1*  5/2014  Nadobny ........... A61K 41/0052
                                              703/2
(Continued)

FOREIGN PATENT DOCUMENTS

CN       104519956 A      4/2015
CN       108348770 A      7/2018
(Continued)

OTHER PUBLICATIONS

Soraya Gavazzi , Astrid L. H. M. W. van Lier , Cornel Zachiu , Eric Jansen , Jan J. W Lagendijk , Lukas J. A Stalpers , Hans Crezee & H. Petra Kok (2020) Advanced patientspecific hyperthermia treatment planning, International Journal of Hyperthermia, 37:1, 992-1007, DOI: 10.1080/02656736.2020.1806361 (Year: 2020).*
(Continued)

*Primary Examiner* — Robert A Sorey
(74) *Attorney, Agent, or Firm* — Noréns Patentbyrå Ab

(57)         ABSTRACT

A combined set of treatment plans including radiation treatment and hyperthermia treatment may be optimized either by co-optimizing both plans together or by optimizing one of the plans and then optimizing the other taking into account the predicted effect of the first optimized plan.

16 Claims, 2 Drawing Sheets

(56) References Cited

U.S. PATENT DOCUMENTS

| | | | | |
|---|---|---|---|---|
| 2017/0091409 A1 * | 3/2017 | Jiang | | G16H 30/40 |
| 2017/0216623 A1 | 8/2017 | Parsai et al. | | |
| 2018/0304100 A1 | 10/2018 | Bharat et al. | | |
| 2021/0002338 A1 | 1/2021 | Peyman | | |
| 2021/0020296 A1 * | 1/2021 | Sjölund | | A61N 5/1031 |
| 2021/0228406 A1 * | 7/2021 | Van Den Bossche | | A61F 7/12 |

FOREIGN PATENT DOCUMENTS

| | | | | |
|---|---|---|---|---|
| RU | 2548770 C1 | 4/2015 | | |
| WO | WO-2012159043 A2 * | 11/2012 | | A61B 5/0071 |
| WO | WO-2013153506 A1 * | 10/2013 | | A61B 5/0036 |
| WO | 2017071965 A1 | 5/2017 | | |
| WO | WO-2022228899 A1 * | 11/2022 | | A61N 5/1031 |
| WO | WO-2023274637 A1 * | 1/2023 | | A61N 5/103 |
| WO | WO-2024147937 A1 * | 7/2024 | | A61N 5/1077 |

OTHER PUBLICATIONS

Bakker A, van der Zee J, van Tienhoven G, Kok HP, Rasch CRN, Crezee H. Temperature and thermal dose during radiotherapy and hyperthermia for recurrent breast cancer are related to clinical outcome and thermal toxicity: a systematic review. Int J Hyperthermia. 2019;36(1):1024-1039. (Year: 2019).*

Kok HP, Crezee J, Franken NA, Stalpers LJ, Barendsen GW, Bel A. Quantifying the combined effect of radiation therapy and hyperthermia in terms of equivalent dose distributions. Int J Radiat Oncol Biol Phys. Mar. 1, 2014;88(3):739-45. (Year: 2014).*

Crezee, H. et al., "Thermoradiotherapy planning Integration in routine clinical practice", Int. Journal of Hyperthermia, Jan. 2, 2016. pps. 41-49.

Kok, H., Petra et al.; "Hyperthermia treatment planning: Clinical Application ond Ongoing Developments", IEEE Journal of Electromagnetics RF and Microwaves in Medicine and Biology, Oct. 21, 2020, pp. 214-222.

International Search Report & Written Opinion dated Aug. 4, 2022, European Patent Office, Rijswijk, Netherlands.

Office Action dated Mar. 29, 2025 in corresponding Chinese application No. 202280023012.9, Chinese Patent Office, Beijing, China.

* cited by examiner

OPTIMIZATION OF THERMORADIOTHERAPY TREATMENT

TECHNICAL FIELD

The present invention relates to the planning of multimodality treatments combining radiation therapy and hyperthermia treatment. Such treatments are often referred to as thermoradiotherapy, or hyperthermia-enhanced radiotherapy.

BACKGROUND

Radiotherapy, or radiation therapy (RT), involves submitting a patient's body to radiation. Hyperthermia therapy (HT) refers to the treatment of malignant diseases by heating the tissue. Various heating techniques may be used, including, but not limited to, liquid agents, capacitive heating systems, exposure by electromagnetic radiation (radiofrequency, microwaves, or infrared), acoustic waves (ultrasound). The use of HT also enhances the effects of RT and some systemic types of treatment, such as chemotherapy. Raising the tumor temperatures to approximately 39-45° C., in combination with RT and/or systemic therapies has been found to increase the tumor control probability (TCP) compared to single modality treatments, and with practically no increase in late normal tissue complication probability (NTCP). This synergistic effect is due to various sensitization effects of HT, which include inhibition of DNA repair mechanisms and reoxygenation, as well as direct HT cell kill of radioresistant hypoxic tumor cells and triggering of multiple immune responses. The radiosensitizing effect can be quantified mathematically using known concepts like the equivalent radiation dose (EQD) including temperature-dependent parameters for the radiation, biological models including TCP and NTCP which could be dependent on the temperature-dependent EQD, the thermal enhancement ratio (TER), which is defined as the ratio of the radiation dose needed to produce a specific therapeutic effect without HT treatment, and the radiation dose needed to produce the same therapeutic effect combined with HT treatment.

Normally, different apparatuses are used for the HT treatment and the RT treatment, respectively, and for practical reasons they are therefore usually given sequentially to the patient, with approximately 0-4 h interval between the treatments. The delivery of different treatment modalities can also be simultaneous. RTHT treatments typically consists of approximately 5-35 RT fractions delivered daily, with a HT boost 1-2 times/week resulting in a total of approximately 1-10 HT fractions. Generally, the same RT treatment is delivered independently of whether or not a HT fraction is delivered on the same day, although strategies for adapting the RT plan on the days of HT delivery exist.

The optimization of such multimodality treatment involves the optimization of at least one RT plan and at least one HT plan.

A general aim in all such treatments is to optimize the therapeutic effect of the treatment on the patient. For multimodality treatments, this involves exploiting the synergistic effects as much as possible. For a RTHT treatment, this includes exploiting effects related to co-localization of hot or cold temperature voxels, respectively, with RT doses, to account for the temperature-dependent radiosensitization in each voxel.

Accordingly, international patent application PCT/EP2016/074609 discloses a method of planning hyperthermia-enhanced radiation therapy in which a plan for either hyperthermia therapy or radiation therapy is first developed. After delivery of this plan to the patient, the result is evaluated and taken into account when optimizing the other plan. In other words, the hyperthermia treatment plan is optimized and delivered, and the radiation treatment plan is optimized taking the result of the delivery into account, or vice versa.

SUMMARY OF THE INVENTION

The disclosure aims to provide an improved planning method for multimodality treatments involving both radiation therapy and hyperthermia therapy.

The disclosure relates to a computer-based method for generating a set of treatment plans including a radiation treatment plan and a hyperthermia treatment plan, for thermoradiotherapy treatment for a treatment volume of a patient, the method comprising the steps of:

a. obtaining an optimization problem including at least one objective function related to the multimodality treatment including hyperthermia and radiation, based on a model taking the combined predicted effect of heat and radiation dose into account, b. generating at least one of the radiation treatment plan and the hyperthermia treatment plan by optimizing the optimization function value evaluated for the predicted combined effect over the set of treatment plans.

According to the invention, therefore, the synergistic effects of RTHT treatments can be enhanced, since treatments are optimized and planned together. The invention enables determining a more correct co-location of the temperature distribution, the radiation dose distribution, and optionally the effect of additional systemic therapies in the patient so that the synergistic effects of the treatments can be exploited more efficiently. In preferred embodiments, the radiation treatment plan is an external beam radiation treatment plan.

Issues related to the co-localization of hot or cold temperature voxels with corresponding RT doses can be mitigated, by increasing or reducing the dose in a voxel by accounting for the temperature-dependent sensitization of the radiation dose. In some cases, such issues may even be taken advantage of. For example, a radiation dose to a target may be reduced while maintaining a predetermined TCP if the temperature in the target is increased.

In an OAR a combination of high temperature and high radiation dose should be avoided, because the combination may result in an increased NTCP. This can be achieved by lowering the temperature and/or the radiation dose in the corresponding voxels in sequential optimization strategies, where the quantity of the modality optimized second is adjusted accounting for the combined predicted effect, or in a co-optimization strategy where both modalities are optimized simultaneously. In a target volume, the enhanced effect caused by a combination of high temperature and high radiation dose may be desired. In accordance with this, high temperatures and high radiation doses can be co-localized to the same voxel(s) within the target volume of the multimodality treatment to enhance the TCP using both sequential and co-optimization strategies.

Before performing step a), the method may include the step of defining the set of treatment plans including the hyperthermia plan and the radiotherapy plan and at least one other type of plan, such as surgery or a plan for a type of systemic treatment including chemotherapy, immunotherapy and hormone therapy. Alternatively, which plans to optimize are predetermined.

The set of treatment plans may for example comprise at least a first and a second radiotherapy plan, where the first radiotherapy plan is optimized for delivery on the same day as the at least one hyperthermia plan and the second radiotherapy plan is optimized for delivery on the days where another hyperthermia plan or no hyperthermia plan is delivered.

In addition to the RT and HT plans, the set of treatment plans comprises at least one additional therapy plan along with the at least one hyperthermia plan and at least one radiotherapy plan, said at least one additional therapy plan related to a systemic treatment such as chemotherapy.

Co-optimization of HT and RT is advantageous because these types of treatment are known to have a strong direct influence on each other and strong synergistic effects. The set of treatment plans may further include plans for one or more additional types of treatment. These additional types of treatment primarily include systemic therapies such as chemotherapy, hormone therapy and immunotherapy, but may also include surgery.

Three general embodiments have been devised, using the embodiment with one RT plan and one HT plan as an example: generating both the RT and the HT plan simultaneously, generating the RT plan and optimizing the HT plan in view of the predicted result of the RT plan, and optimizing the RT plan in view of the predicted result of the HT plan. In the first case, the method involves the step of generating the at least one of the radiation treatment plan and the hyperthermia treatment plan comprises co-optimization of the hyperthermia plan and the radiotherapy plan, the optimization problem including information on a combined predicted effect of temperature and dose for each voxel. In the second case, a pre-existing radiation treatment plan has been obtained and the step of generating the at least one of the radiation treatment plan and the hyperthermia treatment plan comprises optimizing the hyperthermia plan accounting for the predicted effect of at least one pre-existing radiotherapy plan, wherein the optimization problem includes the predicted effect of the radiation dose for each voxel. In the third case, a pre-existing hyperthermia plan has been obtained before the step of obtaining the optimization problem, and the step of generating the at least one of the radiation treatment plan and the hyperthermia treatment plan comprises optimizing the radiotherapy plan accounting for the predicted effect of at least one pre-existing hyperthermia plan, wherein the optimization problem includes temperature dependence information for the biological parameters for each voxel.

In addition to the one or more objective functions, the optimization problem may also comprise one or more constraints defining parameters that must be maintained during optimization. The optimization problem preferably comprises a biological or a physical objective. The optimization problem may also comprise at least one objective function for machine parameter optimization of one or both of the heat delivery system and the radiation delivery system. The optimization problem may also include at least one constraint related to machine limitations of at least one delivery machine that will be used to deliver hyperthermia treatment and/or radiation treatment as constraints or objectives. In some embodiments, the optimization problem includes a simplified machine model for either the heating system or the RT system for which the parameters are optimized, such as radiation fluence optimization and power optimization for the heating system.

The model used as a basis for the optimization problem may be a biological model. The optimization problem advantageously comprises a biological or a physical objective. The model and the objectives may relate to factors such as radiation dose, temperature, equivalent radiation dose (EQD), equivalent uniform distribution (EUD), biological effective dose (BED) and thermal enhancement ratio (TER) limits to targets and organs at risk (OAR) in the treatment volume, dose or temperature volume histograms (DVH and TVH) limits, probability limits for tumor control probability (TCP), and normal tissue complication probability (NTCP), complication free cure probability, secondary cancer and overall survival, linear energy transfer (LET) limits related to the radiation, the location where the particles stop and/or homogeneity and conformity indices.

Aspects of the invention also relate to a computer program product comprising computer-readable code which when run in a processor will cause the processor to perform the method according to the embodiments discussed above. The computer program product may be stored on non-transitory storage unit. Aspects of the invention also relate to a computer comprising a processor and a program memory, wherein the program memory holds such a computer program product for being executed in the processor.

LIST OF ACRONYMS

The following acronyms are used in this document:
BED—biological effective dose
DVH—dose-volume histogram
EQD—equivalent radiation dose
EQD2—equivalent radiation dose in 2-Gy fractions
EUD—equivalent uniform dose
HT—hyperthermia therapy
LET—linear energy transfer
LQ—linear-quadratic
NTCP—normal tissue complication probability
OAR—organ at risk
RT—radiotherapy
RTHT—thermoradiotherapy
TCP—tumor control probability
TER—thermal enhancement ratio. The ratio between the radiation dose required without HT and the radiation dose required for the same situation with HT
TVH—temperature volume histogram.

BRIEF DESCRIPTION OF DRAWINGS

The invention will be described in more detail in the following, by way of examples and with reference to the appended drawings.

DETAILED DESCRIPTION OF EMBODIMENTS

The methods according to embodiments of the invention relate to optimization of treatment plans. As is known in the art, such optimization is performed by applying an optimization problem that has been designed for the situation at hand, based on clinical goals and one or more biological models. The optimization problem is defined by objective functions, which define goals that the optimization should strive towards, for example minimizing dose to tissue surrounding a target, and constraints, which place absolute requirements, for example a minimum dose to the target. Constraints may also reflect machine limitations of at least one delivery machine that will be used to deliver hyperthermia treatment and/or radiation treatment. The skilled person is acquainted with such constraints, which include maximum speed of mechanical parts, maximum radiation delivery per time unit, and other limitations.

Figures 1, 2:
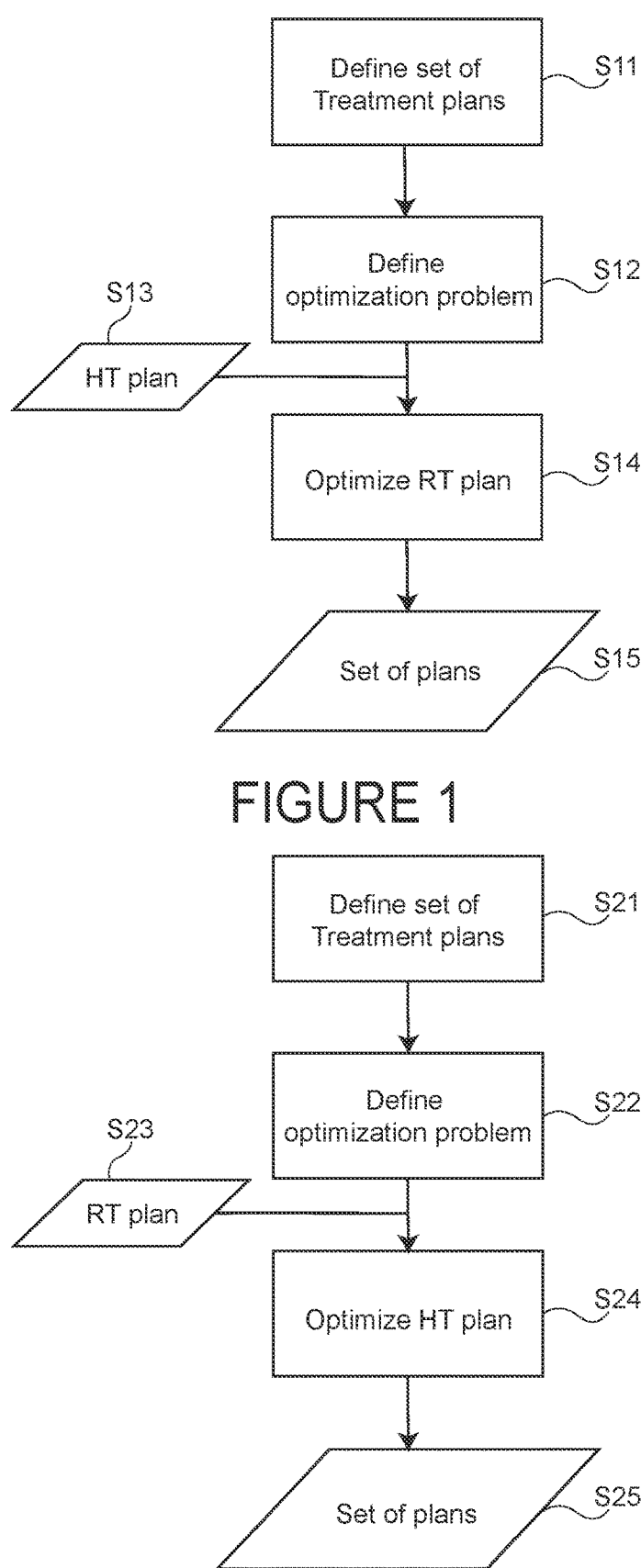
FIGS. 1, 2, 3 are flow charts illustrating different embodiments of a method according to the invention.

FIG. 1 is a flow chart detailing a method according to a first embodiment of the disclosure, in which an RT plan is optimized considering the predicted effect of an HT plan that has been obtained in advance. In a first step S11, a thermoradiotherapy treatment is defined as a set of treatment plans corresponding to the treatment modalities involved. The set of plans in this embodiment includes a hyperthermia plan and a radiotherapy plan and may optionally also include plans of other modalities, such as surgery, immunotherapy, hormone therapy or chemotherapy. At this stage, the following information may be needed:

the planned temperature distribution to result from HT, the time interval between the delivery of the two treatment modalities, if included in the model, the number of HT fractions and the delivery schedule, if not included in the optimization.

In a second step, S12, an optimization problem is obtained for optimizing the set of plans together. To achieve this, in general, the optimization problem must include at least one objective function related to the combined treatment including hyperthermia and radiation, and optionally the other plan or plans included in the set. In this embodiment, the optimization problem comprises optimization functions where the temperature dependence of the biological parameters is included for each voxel of interest.

For example, the equivalent radiation dose (EQD) in 2-Gy fractions (EQD2) of the multimodality treatment could be optimized using the linear-quadratic (LQ) model for cell survival. The LQ-parameters a and B are known to vary with temperature as an increased temperature increase the radiosensitivity. By incorporating models for the temperature dependency of the LQ-parameter it is possible to optimize directly on the EQD2 for the combined predicted therapeutic effect of radiation dose and temperature. Objectives may be set for, for example, maximum/minimum EQD2, DVH limits as well as uniform EQD2. As a further development, EQD2 could be incorporated in one or more suitable models for optimization. Such models include equivalent uniform dose (EUD), tumor control probability (TCP) and normal tissue complication probability (NTCP) models. This could include using objective functions defined based on EQD2, including temperature dependency. It could also include using objective functions defined as models that are based on EQD2, including temperature dependency. In this manner the temperature dependent EQD2, EUD, TCP and/or NTCP will be optimized to fulfil the stated clinical goals.

A pre-existing temperature distribution of a hyperthermia plan is used as input for the optimization of a radiotherapy plan, and in step S14, the RT plan is optimized while considering the radiosensitization caused by the temperature distribution resulting from the pre-existing HT plan S13. The output S15 of step S14 is the set of plans including the pre-existing HT plan and the RT plan optimized using the optimization problem obtained in step S13. Modifications of the order of delivery, or of the number of fractions of the HT plan may be made to enhance the combined effect of RT and HT.

FIG. 2 is a flowchart of a second embodiment of the method according to the invention, in which an HT plan is optimized while considering the combined effect with the radiation dose distribution resulting from a pre-existing RT plan. In a first step S21, a thermoradiotherapy treatment is defined as a set of treatment plans corresponding to the modalities of treatment involved. As for FIG. 1, the set of plans includes a hyperthermia plan and a radiotherapy plan and may optionally also include other types of plans, such as surgery, immunotherapy, hormone therapy or chemotherapy, or a second radiotherapy plan related to a different type of radiotherapy.

In a second step, S22, an optimization problem is obtained for optimizing the set of plans together. To achieve this, the optimization problem must include at least one objective function related to the combined treatment including hyperthermia and radiation, and optionally the other plan or plans included in the set. In this embodiment, the objective function comprises optimization functions where the effect of the radiation dose resulting from the previously obtained radiotherapy plan is included for each voxel of interest. As in the method of FIG. 1, optimization strategies using e.g., EQD2, TCP, and NTCP models could be used for the optimization of the hyperthermia plan.

A pre-existing dose distribution of a radiotherapy treatment plan is used as input for the optimization of a hyperthermia treatment plan, and in step S24, the HT plan is optimized while taking into account the dose distribution resulting from the pre-existing RT plan. The output S25 of step S24 is the set of treatment plans including the previously obtained RT plan and the HT plan optimized using the optimization problem obtained in step S22.

Figure 3:
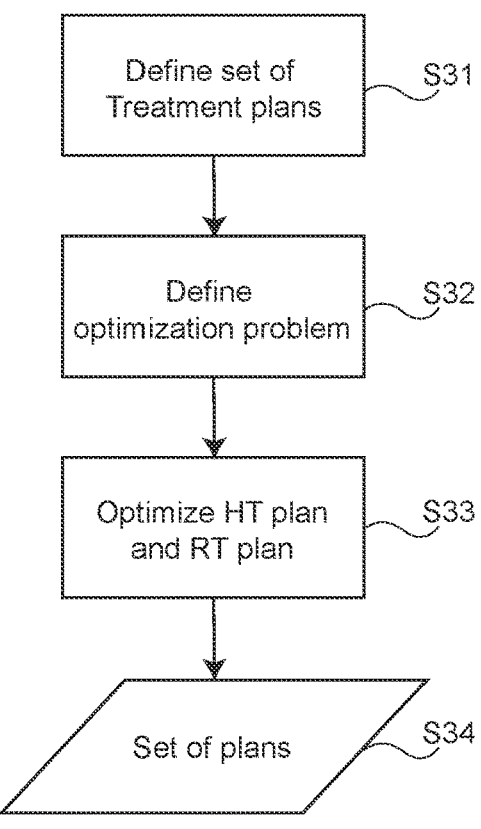

A third embodiment of the inventive method is shown in FIG. 3. In a first step S31, a thermoradiotherapy treatment is defined as a set of treatment plans corresponding to the types of treatment involved. As in the previous embodiments, the set of plans includes one or more hyperthermia plans and one or more radiotherapy plans and may optionally also include other types of plans, such as surgery, immunotherapy, hormone therapy or chemotherapy.

In a second step, S32, an optimization problem is obtained for optimizing the set of plans together. To achieve this, the optimization problem must include at least one objective function related to the combined treatment including hyperthermia and radiation, and optionally the other plan or plans included in the set. In this embodiment, the objective function comprises optimization functions where the predicted combined effect of temperature and dose are included for each voxel of interest. As in the embodiments discussed above, optimization strategies using e.g., EQD2, EUD, TCP, and NTCP models could be used; however, in this embodiment the temperature and dose distributions are simultaneously co-optimized in the search for the optimal treatment in terms of the combined predicted therapeutic effect.

In step S33, the HT plan and the RT plan are optimized in one optimization operation. The output S34 of step S33 is the set of treatment plans including the HT plan and the RT plan optimized together using the optimization problem obtained in step S32.

The first step of each of the methods above, S11, S21, S31 may in many cases not be needed. It may be predefined which treatment plans are to be included, or the possible types of treatment may be restricted by the available equipment, for example. Co-optimization of HT and RT is advantageous because these types of treatment are known to have a strong direct influence on each other and strong synergistic effects.

In each of the methods discussed in connection with FIGS. 1, 2, 3 above, the step of obtaining the optimization problem may include retrieving an existing optimization problem or defining a new optimization problem, or adapting a predefined optimization problem to a specific situation by including or modifying objective functions and/or constraints.

Also, in each of the methods discussed above, two radiotherapy plans may be included in the set of treatment plans in addition to the hyperthermia treatment plan. Including two separate radiotherapy plans may be useful in the cases where two different types of radiation treatment should be combined. It is also possible to include a first radiotherapy plan including the fractions to be delivered in conjunction with hyperthermia treatments, and a second radiotherapy plan including the fractions to be delivered without the effect of hyperthermia treatment. In conjunction within this context means so near in time that the effects of the radiation and the hyperthermia overlap and enhance each other.

Figure 4:
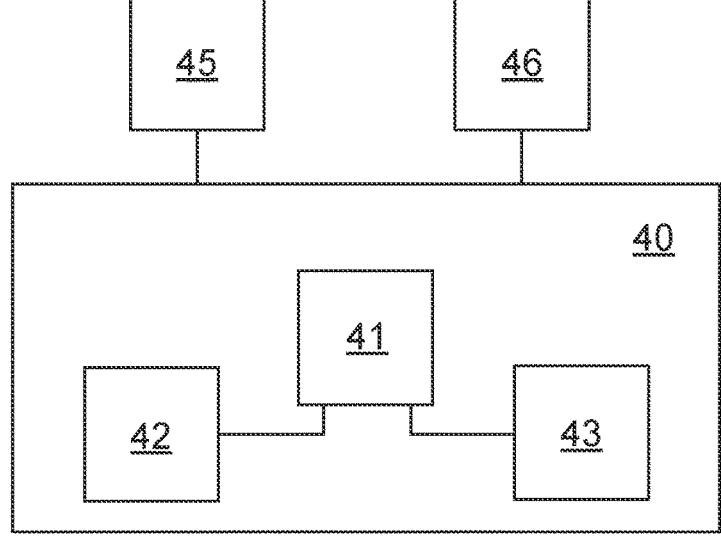
FIG. 4 is a schematic illustration of a computer system in which the method may be performed.

FIG. 4 shows schematically a computer 40 in which the methods according to the invention may be performed. As is common in the art, the computer 40 comprises a processor 41, a program memory 42 and a data memory 43. As will be understood, the program and data memories 42, 43 may be implemented in any suitable way, in the form of one or more memories, internally or externally to the computer 40. The computer comprises, or is connected to, one or more user input/output devices, such as a screen, a keyboard, a mouse, audio input/output means, and any other suitable devices. The program memory 42 holds a computer program arranged to be run in the processor 41 to perform a method according to the invention, for example according to one of the embodiments discussed above. The data memory 43 or memories hold input data to be used in the method, such as patient data, information about the set of plans and, in the case of FIGS. 1 and 2, of the previously obtained plans used as input to the optimization. The data memory 43 may also hold the resulting set of plans that forms the output from the method.

The treatment plans may be planned for delivery by any suitable type of delivery equipment. As mentioned above, different apparatuses are normally used for delivery of HT and RT, respectively. The HT delivery apparatus may use any suitable technique, including, but not limited to, liquid agents, capacitive heating systems, exposure by electromagnetic radiation, acoustic waves (ultrasound), and magnetic HT where nanoparticles are injected in the tumor and subsequently heated by varying magnetic field over the tumor region. Electromagnetic radiation is often used and may include of electromagnetic radiation of any suitable wavelength, including radiofrequency, microwaves, or infrared.

The RT delivery apparatus is preferably an external beam radiation therapy device, for delivering any type of radiotherapy to a patient, including photon, electron or ion radiotherapy. Delivery apparatuses for both RT and HT are well known in the art and will not be discussed in more detail here. Also, the skilled person is familiar with apparatuses and equipment used for other types of treatments, such as surgery and systemic treatments, and their effects. Systemic treatments include chemotherapy, hormone therapy and immunotherapy, all of which are commonly used in the treatment of, for example, cancer patients.

The invention claimed is:

1. A computer-based method for generating a set of treatment plans including a radiation treatment plan and a hyperthermia treatment plan, for thermoradiotherapy treatment for a treatment volume of a patient, the method comprising:

a. obtaining an optimization problem including at least one objective function related to the multimodality treatment including hyperthermia and radiation, wherein the objective function models a combined biological effect of temperature and dose for each of a plurality of voxels of the treatment volume using a biophysical model with temperature-dependent parameters and is subject to constraints of at least one radiotherapy delivery device and at least one hyperthermia applicator;

b. generating at least one of the radiation treatment plan and the hyperthermia treatment plan by optimizing the objective function value evaluated for the predicted combined effect over the set of treatment plans wherein the optimization simultaneously adjusts hyperthermia power deposition parameters and radiation dose-distribution variables within a single coupled optimization problem, such that the temperature field and radiation dose at the voxels evolve interdependently during the optimization; and c. delivering thermoradiotherapy treatment to the patient in accordance with the set of treatment plans.

2. The method of claim 1, wherein the radiation treatment plan is an external beam radiation treatment plan.

3. The method of claim 1, wherein the step of generating the at least one of the radiation treatment plan and the hyperthermia treatment plan comprises co-optimization of the hyperthermia plan and the radiotherapy plan, the optimization problem including information on a predicted combined effect of temperature and dose for each voxel.

4. The method of claim 1, wherein a pre-existing hyperthermia plan has been obtained before the step of obtaining the optimization problem, and wherein the step of generating the at least one of the radiation treatment plan and the hyperthermia treatment plan comprises optimizing the radiotherapy plan accounting for the predicted effect of at least one pre-existing hyperthermia plan, wherein the optimization problem includes temperature dependence information for the biological parameters for each voxel.

5. The method of claim 1, wherein a pre-existing radiation treatment plan has been obtained and wherein the step of generating the at least one of the radiation treatment plan and the hyperthermia treatment plan comprises optimizing the hyperthermia plan accounting for the predicted effect of at least one pre-existing radiotherapy plan, wherein the optimization problem includes the effect of the radiation dose for each voxel.

6. The method of claim 1, wherein the model includes one or more of the following: the equivalent radiation dose, equivalent uniform distribution, biological effective dose, thermal enhancement ratio, tumor control probability, normal tissue complication probability, complication free cure probability, secondary cancer, and/or overall survival.

7. The method of claim 1, wherein the optimization problem comprises constraints which define parameters that are maintained during optimization.

8. The method of claim 1, wherein the optimization problem comprises a biological or a physical objective.

9. The method of claim 1, wherein the optimization problem is defined to optimize machine parameters of at least one of the heat delivery systems and the radiation delivery system as variables.

10. The method of claim 1, wherein the optimization problem includes at least one constraint related to machine limitations of at least one delivery machine that will be used to deliver hyperthermia treatment and/or radiation treatment as constraints or objectives.

11. The method of claim 1, wherein the optimization problem includes a simplified machine model for either the heating system or the radiation treatment system for which the parameters are optimized.

12. The method of claim 1, further comprising the step, performed before the steps of claim 1, of defining the set of treatment plans including the hyperthermia plan and the radiotherapy plan and at least one other type of plan.

13. The method of claim 1, wherein the set of treatment plans comprises at least a first and a second radiotherapy plan, where the first radiotherapy plan is optimized for delivery on the same day as the at least one hyperthermia plan and the second radiotherapy plan is optimized for delivery on the days where no hyperthermia plan is delivered.

14. The method of claim 1, wherein the set of treatment plans comprises at least one additional therapy plan along with the at least one hyperthermia plan and at least one radiotherapy plan, said at least one additional therapy plan related to a systemic treatment.

15. A computer program product comprising a non-transitory computer readable storage medium containing instructions which when run in a processor will cause the processor to perform the method according to claim 1.

16. A computer comprising a processor and a program memory, wherein the program memory holds a computer program product according to claim 15, for being executed in the processor.

\* \* \* \* \*